United States Patent [19]
Menken et al.

[11] Patent Number: 5,800,461
[45] Date of Patent: Sep. 1, 1998

[54] CONSTANT CHARGE TIME OF DEFIBRILLATION CAPACITOR

[75] Inventors: John Menken, Champlin, Minn.; Paul Monroe, Janesville, Wis.

[73] Assignee: Cardiac Pacemakers, Inc., St. Paul, Minn.

[21] Appl. No.: 538,831

[22] Filed: Nov. 13, 1995

Related U.S. Application Data

[63] Continuation of Ser. No. 344,611, Nov. 18, 1994, abandoned, which is a continuation of Ser. No. 978,549, Nov. 19, 1992, abandoned.

[51] Int. Cl.⁶ .................................................. A61N 1/39
[52] U.S. Cl. .................................................. 607/7; 607/62
[58] Field of Search ........................... 607/4, 5, 7, 8, 607/62, 63, 74; 128/704; 600/517

[56] References Cited

U.S. PATENT DOCUMENTS

| | | | |
|---|---|---|---|
| 3,226,630 | 12/1965 | Lampke | 323/66 |
| 3,376,489 | 4/1968 | Crayton. | |
| 3,383,584 | 5/1968 | Atherton | 323/4 |
| 3,547,127 | 12/1970 | Anderson | 128/421 |
| 3,746,005 | 7/1973 | Thaler et al. | 128/419 |
| 3,746,006 | 7/1973 | Thaler | 128/419 |
| 3,757,795 | 9/1973 | Anderson | 128/419 |
| 3,759,265 | 9/1973 | Thaler et al. | 128/419 |
| 3,782,389 | 1/1974 | Bell | 128/419 D |
| 3,835,368 | 9/1974 | Williams | 323/17 |
| 3,867,949 | 2/1975 | Schwalm et al. | 128/419 |
| 4,015,609 | 4/1977 | Mensink et al. | 128/419 |
| 4,056,105 | 11/1977 | Ravas | 128/419 |
| 4,119,903 | 10/1978 | Pirkle | 128/419 D |
| 4,120,306 | 10/1978 | Renirie | 128/419 |
| 4,233,659 | 11/1980 | Pirkle | 128/419 D |
| 4,345,604 | 8/1982 | Renirie | 128/419 |
| 4,345,606 | 8/1982 | Littleford | 128/784 |
| 4,360,026 | 11/1982 | Venin et al. | 128/419 D |
| 4,437,466 | 3/1984 | Saulson et al. | 128/419 |
| 4,548,209 | 10/1985 | Wielders et al. | 607/4 |
| 4,586,118 | 4/1986 | Mihalka | 363/17 |
| 4,590,941 | 5/1986 | Saulson et al. | 128/419 |
| 4,599,523 | 7/1986 | Pless et al. | 307/31 |
| 4,800,883 | 1/1989 | Winstrom | 128/419 D |
| 5,097,830 | 3/1992 | Eikefjord et al. | 607/8 |
| 5,163,428 | 11/1992 | Pless | 128/908 |
| 5,237,989 | 8/1993 | Morgan et al. | 607/5 |

FOREIGN PATENT DOCUMENTS

| 0272021 | 7/1964 | Australia | 607/5 |
|---|---|---|---|

*Primary Examiner*—William E. Kamm
*Assistant Examiner*—Kennedy J. Schaetzle
*Attorney, Agent, or Firm*—Evenson, McKeown, Edwards & Lenahan, P.L.L.C.

[57] ABSTRACT

A capacitor charging circuit for charging a defibrillation capacitor in a constant period of time regardless of battery voltage by employing a controlled duty cycle charging technique. The defibrillation capacitor is charged in a piecemeal manner through a transistor and flyback transformer circuit. The gate of the transistor is driven by a constant frequency pulse train inverter drive signal in which voltage is conveyed to the capacitors during one-half of the full cycle of the pulse train. The primary of the transformer is controlled by each pulse of the inverter drive signal so that the secondary of the transformer supplies current to the defibrillation capacitors during the off half cycle of the drive signal, the charge being built up in the defibrillation capacitors incrementally during the off half cycle of the inverter drive signal until the predetermined voltage is reached.

2 Claims, 4 Drawing Sheets

CONSTANT CHARGE TIME OF DEFIBRILLATION CAPACITOR

This is a continuation application of Ser. No. 08/344,611, filed on Nov. 18, 1994, which is a continuation of Ser. No. 07/978,549, filed Nov. 19, 1992, both now abandoned.

BACKGROUND OF THE INVENTION

The present invention relates to implantable cardiac devices and more specifically to a system for charging a defibrillation capacitor.

In implantable devices, such as defibrillators, it is necessary to charge a capacitor to a desired level which is then discharged to generate a defibrillation pulse. A battery is provided in the implantable device to supply the energy for charging the capacitor. As the battery becomes depleted, it has been found that a longer time is required to charge the capacitor. It is well known in the medical community that the longer it takes to defibrillate once fibrillation onsets, the lesser are the chances for recovery and survival. There continues to be a problem between the battery voltage and charge time of the substantially large capacitors used in defibrillation.

Systems are known for charging a capacitor. For example, U.S. Pat. No. 4,586,118 to Mihalka discloses a capacitor charging circuit having means to compensate for changes in the capacitive load as the capacitor is charged to maintain a constant peak charging current irrespective of the capacitive load changes. However, the system disclosed by Mihalka does not compensate for variations in the power supply.

In the field of implantable cardiac treatment devices, attempts have been made to compensate for depleted batteries. U.S. Pat. Nos. 4,599,523 to Pless et al., 4,590,941 to Saulson et al., 3,547,127 and 4,437,466 to Anderson, 3,759, 265 and 3,746,005 to Thaler et al., 4,056,105 to Ravas, and 4,345,604 and 4,120,306 to Renirie disclose such systems in implantable cardiac pacer devices. The Pless et al. patent discloses a priority switching circuit for providing a minimum voltage to a voltage sensitive load while charging a capacitor so that a battery supply is connected to the capacitor whenever the voltage across the capacitor drops below a preset value. The switching frequency varies with the internal impedance of the battery.

The Saulson et al. and ('466) Anderson patents disclose cardiac pacer systems having auxiliary or emergency batteries to maintain constant pulse generation techniques when the main battery becomes depleted. The ('127) Anderson patent discloses a cardiac pacemaker having a regulated power supply to provide a current independent of supply voltage over a large range of supply voltages.

The Thaler et al. and Ravas patents disclose electronic circuits to maintain a constant pulse width regardless of energy source variations in pacemaking systems.

The Renirie patents disclose cardiac pacers having power source interface and switching circuits to achieve maximum utilization of available source energy. Specifically, a DC conversion circuit is provided to raise the value of the source voltage to desirable values as a function of the source voltage for driving an entire circuit or portions of a circuit.

In the field of implantable cardioversion, by contrast to pacing, it is necessary to charge a capacitor to relatively high energy levels, one system has been developed to prevent loading down supply voltage to other circuitry. Specifically, U.S. Pat. No. 4,548,209 to Wielders et al. discloses an implantable cardioverter having charging circuitry including a supply voltage detector which alters the time period of a timing circuit to regulate the amount of current drawn by the primary of a transformer; the secondary of the transformer being connected to a cardioversion capacitor.

However, there is no system heretofore known which operates to provide a constant charge time for a defibrillation capacitor over substantially the entire life of the finite battery supply.

SUMMARY OF THE INVENTION

It is a primary object of the present invention to eliminate battery voltage as a factor of defibrillation capacitor charge time.

It is a further object of the present invention to charge a defibrillation capacitor in a substantially constant period of time over substantially the entire viable life of a battery.

The present invention comprises circuitry for charging defibrillation capacitors in a constant period of time regardless of battery voltage by employing a controlled duty cycle charging technique. The defibrillation capacitors are charged in a piecemeal manner through a transistor and flyback transformer circuit. The gate of the transistor is driven by a constant frequency pulse train in which voltage is conveyed to the capacitors during one-half of the full cycle of the pulse train. The product of the current and the voltage delivered to the capacitors (voltage×current) is constant. Therefore, the current increases as the voltage decreases and thus the charge time is constant because the power is constant.

By providing a constant charging time, several advantages are achieved. The viable life of the battery is increased because less average current is drained from the battery. In addition, because smaller average, as well as peak currents are used, the associated circuit components may be smaller in size decreasing overall size of the implantable package. A further consequence of smaller currents is reduced heat generation and thus improved reliability. Further yet, because charge time is constant, there is no need to perform diagnostic follow up procedures on the capacitor charge. Finally, by selecting a suitable charge time and holding it constant when the battery is at full charge as well as at further depleted levels, the probability of survival may increase over the viable life of the battery. Still another advantage is the use of a fixed charging frequency. A fixed charging frequency is easier to isolate with a detector serving to detect the charge signal.

DETAILED DESCRIPTION OF THE DRAWINGS

Figure 1:
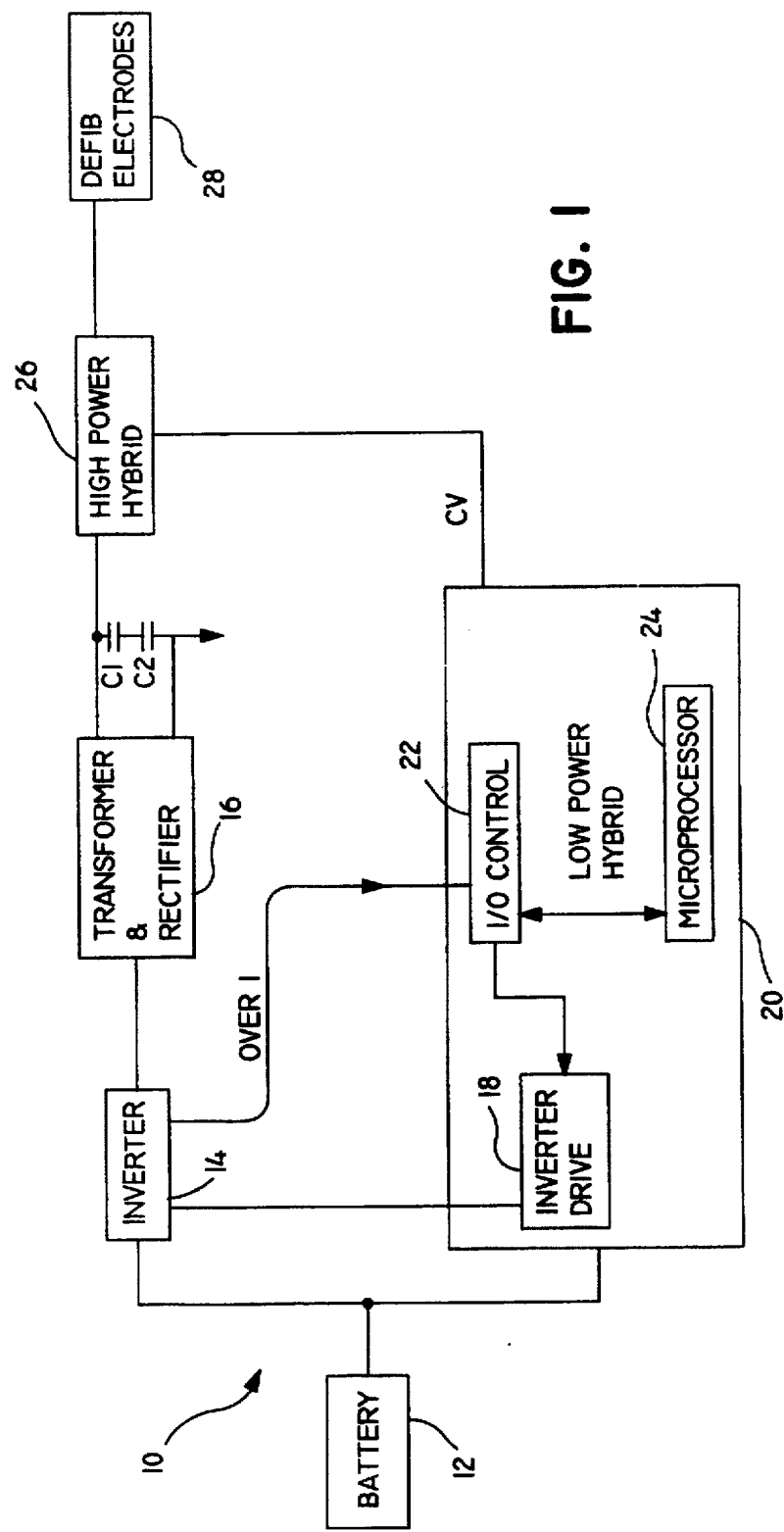
FIG. 1 is a block diagram of the circuitry associated with the constant charge time system of the present invention.

Referring first to FIG. 1, the constant charge time system of the present invention is generally shown at 10. The primary purpose of the system 10 is to charge the defibrillation capacitors C1 and C2 by way of the battery 12. While two capacitors are shown, it is possible to employ the present invention for charging one or more than two capacitors. Specifically, it is desirable to charge the capacitors C1 and C2 at a substantially constant rate over the entire life of the battery 12.

In this regard, an inverter circuit 14 and transformer 16 are provided between the battery 12 and the capacitors C1 and C2. The inverter 14 is driven by an inverter drive circuit 18 formed as part of a low power hybrid circuit 20. As will be described in more detail hereinafter, the inverter 14 essentially comprises a transistor switch which is repeatedly triggered to supply power from the battery 12 to a primary of the transformer 16. A secondary of the transformer 16 is charged by the primary which in turn charges the capacitors C1 and C2.

The drive frequency of the inverter 14 is controlled by the inverter drive circuit 18. In turn, the inverter drive circuit 18 is directly controlled by the I/O control circuit 22 via the microprocessor 24. The I/O control circuit 22 monitors, among other things, the voltage level on the defibrillation capacitors C1 and C2 to terminate the delivery of an inverter drive signal from the drive circuit to the inverter 14, when the microprocessor programmed charge on C1 and C2 has been reached.

The high power hybrid circuit 26 is provided to gate the voltage charged on the defibrillation capacitors C1 and C2 to the defibrillation electrodes shown at 28. Microprocessor 24 is responsive to parameters related to cardiac activity for controlling the high power hybrid to pass the capacitor voltage to the defibrillation electrodes 28.

Figure 2:
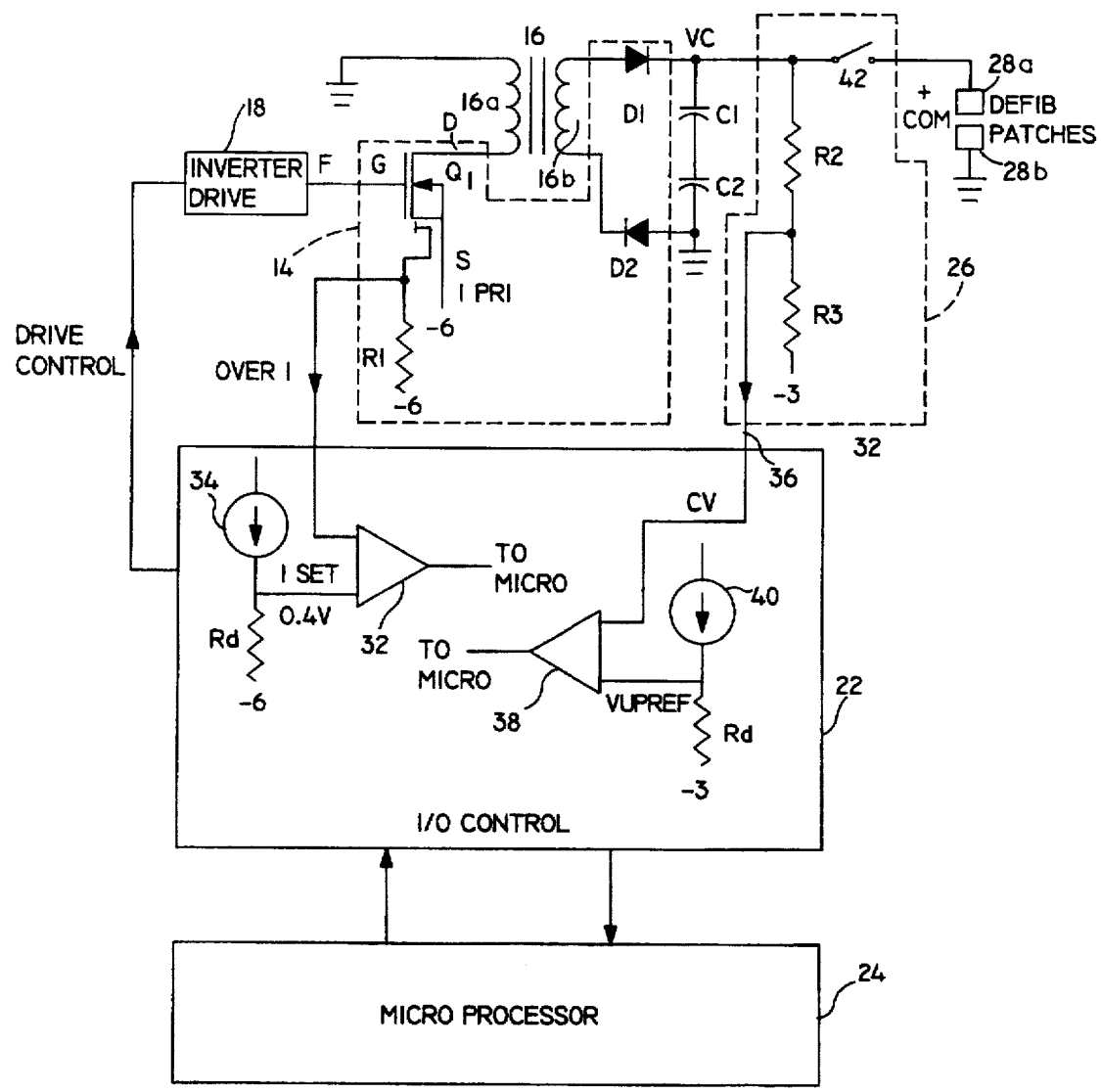
FIG. 2 is a schematic diagram of the inverter circuitry of the constant charge time system of the present invention.

Turning now to FIG. 2, the inverter 14, high power hybrid 26, and I/O control unit 22 are shown in more detail in connection with the defibrillation capacitors C1 and C2. The inverter drive 18, still shown in block form, is connected between the I/O control unit 22 and the inverter unit 14. Generally, the inverter 14 comprises an FET transistor Q1, which may be, for example, model No. MTP10N10M sold by Motorola Corporation. The inverter drive 18 controls the state of the transistor Q1 for selectively supplying current through the drain D of the transistor Q1 to the primary 16a of the transformer 16. Specifically, the inverter drive 18 supplies pulses in the form of an inverter drive signal at a preset frequency F to the gate G of the transistor Q1 to turn the transistor Q1 on. In an ON state, the transistor Q1 supplies current to the primary 16a while in an OFF state, no current is supplied to the primary 16a. A pulse supplied by the inverter drive 18 is terminated when the current in the mirror resistor R1 reaches a preset value.

The current in the mirror resistor R1 which is connected to the source of the transistor Q1 is fed to the I/O control unit 22 so that it may be continuously compared with a preset value. In this regard, the I/O control unit 22 includes a comparison amplifier 32, a current source 34, and resistor $R_d$ connected to a source of −6 volts. The current sensed from the mirror resistor R1 is connected to one terminal of the amplifier 32 and the other terminal of the amplifier senses voltage (VUPREF) from the node between the current source 34 and divider resistor $R_d$.

Inverter 14 also includes rectifier diodes D1 and D2 to ensure that current built up in the secondary 16b of the transformer 16 charges the capacitors C1 and C2 to generate a voltage which is positive at the node VC with respect to the ground terminal connected to one terminal of the capacitor C2.

The high power hybrid circuit 26 includes, among other sub-circuits not shown in FIG. 2, two resistors R2 and R3 and switch 42. Resistor R2 is of a substantially large value, such as 10 M ohms while resistor R2 is of a substantially small value, and can be trimmed to achieve an accurate ratio between R2 and R3. Resistor R3 is connected to a −3 volt source at one terminal thereof. The voltage between resistors R2 and R3 is tapped and fed to the I/O control circuit 22 via line 36. The voltage on line 36 is the voltage across the capacitors C1 and C2 and is termed CV. I/O control unit 22 includes a comparison amplifier 38, a current source 40 and resistor $R_d$. The line 36 carrying the signal CV is connected to one input of the comparator 38 and the other input terminal of the comparator 38 is connected between the current source 40 and the resistor $R_d$.

The output signals of comparators 32 and 38 are fed to the microprocessor 24 for further processing as will be explained in more detail hereinafter. Generally, however, the microprocessor 24 will cause the inverter drive 18, via I/O control circuit 22, to stop delivering drive pulses to the inverter 14 once the voltage on the defibrillation capacitors has reached the value programmed by the microprocessor by monitoring the signal CV. This is done via the DRIVE CONTROL signal shown in FIG. 2.

When it is desired to discharge the voltage stored on the defibrillation capacitors C1 and C2, the microprocessor generates a signal which closes the switch 42 in the high power hybrid circuit 26. Once switch 42 is closed, the voltage across the defibrillation capacitors is supplied to one of the defibrillation electrodes 28a and 28b against the other so that an electric field is generated throughout the heart between the electrodes 28a and 28b.

Figure 3:
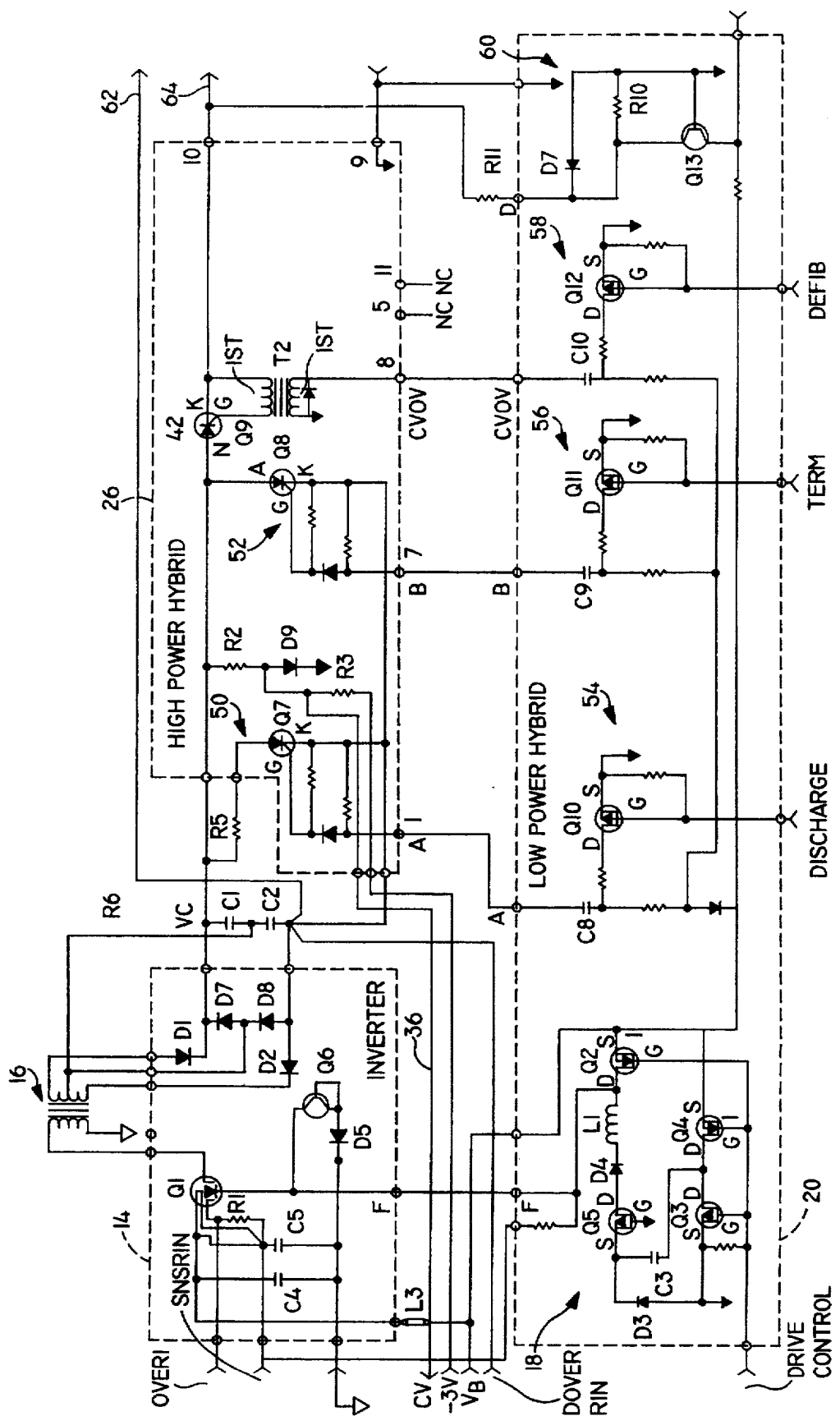
FIG. 3 is a detailed schematic diagram of a portion of the circuitry illustrated in FIG. 1.

FIG. 3 illustrates the inverter 14, inverter drive 18 and high power hybrid 26 in more detail. (The low power hybrid 20 is shown without the I/O control circuit 22 in FIG. 3 for simplicity.) The battery is represented as $V_B$ and is connected to the source of the transistor Q1 and to the inverter drive 18. The gate of transistor Q1 requires 10 volts or more to ensure low on resistance characteristics. Because the drive signal supplied by I/O control 22 can go as low as 3 volts under transient conditions, a gate boost circuit is necessary. In this regard, the inverter drive 18 comprises transistors Q3 and Q4 which are connected so as to form a complimentary inverter for the drive signal. Capacitor C3 and diode D3 form a polarity inverter. Diode D4 and inductor L1 are connected in series with transistor Q5 and form a LC voltage doubler with the gate to source capacitance of Q1.

Under control of the DRIVE CONTROL signal, whenever transistor Q4 is turned on, capacitor C3 is charged to the supply voltage. On the other hand, when Q4 is turned off and Q3 is turned on, the polarity of capacitor C3 is reversed and the drain of Q4 is grounded. Consequently, the inverted (positive rather than negative) supply voltage is applied to the source of transistor Q5 to turn this transistor on. The combination of diode D3 and inductor L1 guarantee that the gate of transistor Q1 is driven positive with respect to the source at least three times the value of the supply voltage because the source is at a negative potential.

As shown in FIG. 3, the inverter 14 further includes capacitors C4 and C5 which together with the inductor L3 form a filter to prevent high frequency current from flowing into the battery. Transistor Q6 is connected across the gate of transistor Q1 and together with diode D5 ensure that the actual gate voltage does not exceed 10 volts with respect to ground so that the gate of the transistor Q1 is protected when the battery is fresh (at full capacity). Transistor Q2 returns the gate of transistor Q1 to $V_B$ to ensure that it turns off quickly.

The transformer 16 is a flyback transformer sized to allow operation at a constant charge time over a wide supply range. The charge time is chosen to be approximately 10 seconds with a new battery which is assumed to put out 6.4 volts under no load. The required inductance of the primary may be derived according to the charge time chosen for maximum battery output. It has been found that the required primary inductance is 10 microhenries. The smallest possible core for the application of this transformer is an RM4 core preferably formed of TDK H7C1 material which has a Bsat of 4000 gauss at 40 degrees Celsius.

The secondary circuit of the transformer 16 and the capacitors C1 and C2 are charged in parallel even though they are connected in series with respect to the switch 42 of the high power hybrid 26. As a result, there is no need to "balance" the capacitors to provide even voltage distribution. When the capacitors are discharged, diodes D7 and D8 insure that the larger of the two capacitors does not reverse the polarity of the smaller capacitor.

The high power hybrid circuit 26 is designed to convey the charge on the capacitors C1 and C2 to the defibrillation electrodes 28a and 28b when the microprocessor issues a defibrillation control signal. Discharge sub-circuit 50 includes a transistor Q7 and resistor R5 which form a discharge path for the stored energy on the capacitors C1 and C2 in the event that it is necessary to discharge the capacitors without delivering a pulse to the patient. Sub-circuit 50 includes an SCR Q7 (silicon controlled rectifier) and associated biasing resistor and diode (not labelled) that discharges capacitors C1 and C2 internally if therapy is not required. This is achieved by triggering the SCR Q7 to discharge the capacitors C1 and C2 through resistor R5. Terminate sub-circuit 52 includes an SCR Q8 (and associated biasing diode and resistor) for truncating the defibrillation pulse delivered to the patient by discharging the capacitors C1 and C2 directly to ground. Sub-circuits 50 and 52 are controlled by the low power hybrid 20 as will be explained hereinafter. Resistor R6 limits the discharge current to prevent internal damage.

The switch 42 is embodied as a silicon rectifier Q9, the gate of which is connected to transformer T2. Transformer T2 is provided for firing the SCR Q9.

As aforementioned, the voltage across the capacitors C1 and C2 is sensed through resistors R2 and R3. Diode D9 is provided to protect the system circuits in the event that R3 opens. A negative 3 volt reference is applied to the resistor R3 which is the same as that used as a reference to the comparator 38 via resistor $R_d$ (FIG. 2). Thus, both inputs to comparator 38 are (indirectly) referenced to negative 3 volts to allow current source 40 to be programmed to zero while the comparator still has headroom for operation.

The low power hybrid circuit 20 further includes a discharge driver circuit 54, a terminate driver circuit 56, a defibrillation trigger circuit 58 and a fault detection circuit 60. The discharge driver circuit 54 comprises transistor Q10 and capacitor C8 (together with associated biasing circuit elements). By bringing a signal on the line labelled DISCHARGE low, the SCR Q7 of the discharge circuit 50 is grounded so that the charge on the capacitors C1 and C2 will be diverted through resistor R5 and SCR Q7 of the discharge sub-circuit 50 to ground.

The defibrillation trigger circuit 58 and the terminate driver circuit 56 are used to deliver a defibrillation or cardioversion pulse. The terminate driver circuit 56 comprises a transistor Q11 (and associated gate drive circuit components) which is connected via a capacitor C9 to the terminate sub-circuit 52 in the high power hybrid 26. Similarly, defibrillation trigger circuit 58 comprises a transistor Q12 (and associated gate drive circuit components) which is connected via capacitor C10 to the transformer T2.

When the microprocessor 24 determines that it is necessary to deliver a defibrillation or cardioversion pulse, the signal on the DEFIB line is pulled low. This turns transistor Q12 ON which discharges capacitor C10 through the pulse transformer T2. As a result, SCR Q9 is turned on and the charge on the capacitors C1 and C2 is delivered to the defibrillation electrodes via lines 62 and 64. When the defibrillation pulse reaches approximately ⅓ of its initial value, the signal CV is sensed by the microprocessor through the I/O circuit 22. The microprocessor responds by generating a signal on the TERM line to turn ON transistor Q11. This discharges capacitor C9 through the gate of transistor Q8 which shorts the capacitors C1 and C2 to ground through resistor R6 (approximately 2 ohms).

The fault detection circuit 60 comprises transistor Q13, the emitter of which is connected to a resistor-diode combination R10-D7. The fault detection circuit 60 is connected to the output line 64 in the high power hybrid 26 via resistor R11. In the event that the transistor embodying switch 42 becomes shorted, the output of the charging current would flow through the heart. However, some of this current would also flow through resistor R11 and the emitter-base junction of transistor Q13 bringing the signal of the FAULT line high. The microprocessor senses the status on the FAULT line through the I/O control circuit 22 and shuts down the inverter 14 at once if switch 42 shorts.

Figure 4:
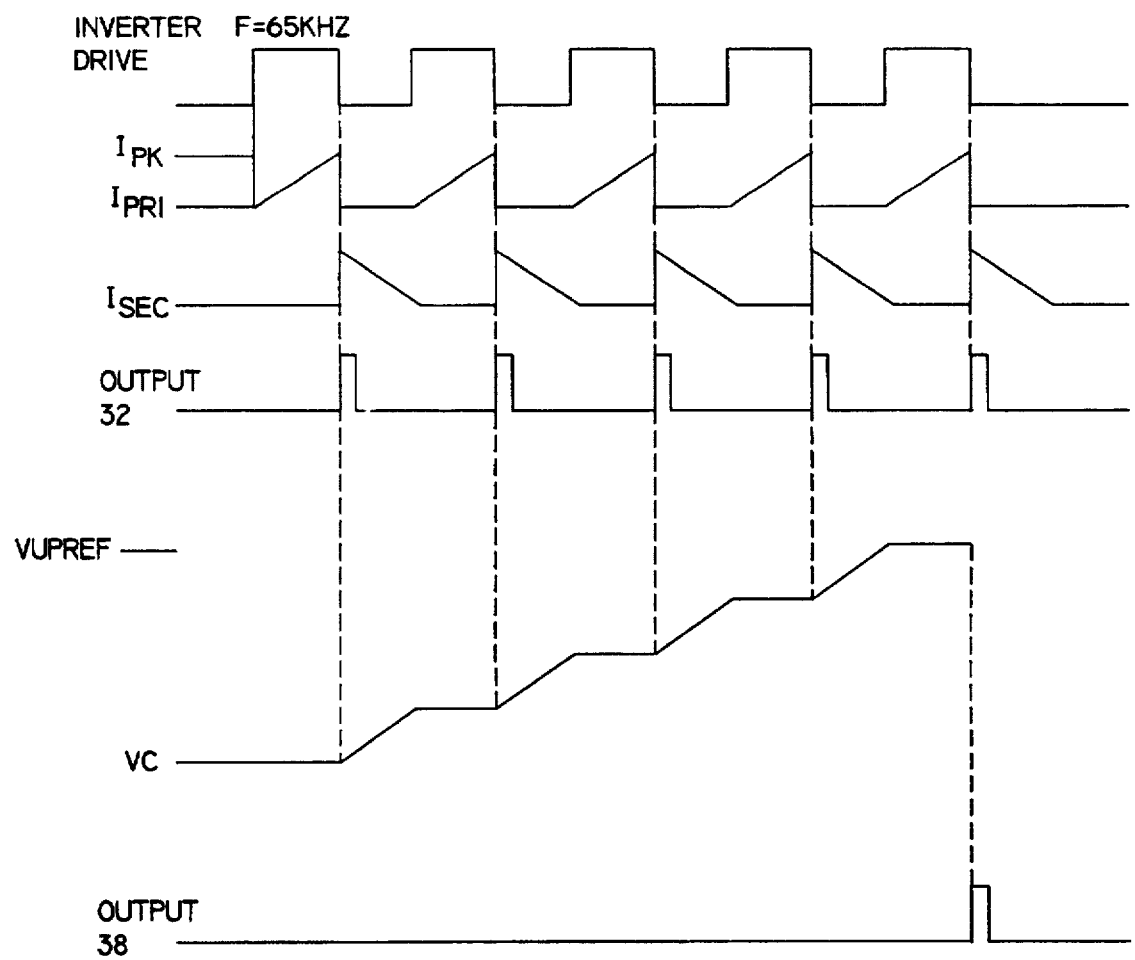
FIG. 4 illustrates the timing of various signals in the constant charge time system of the present invention.

The operation of the constant charge time mechanism will now be described with reference to FIGS. 2, 3 and 4. Generally, the constant charge time mechanism operates by charging the capacitors C1 and C2 in increments by repeatedly charging the primary of the transformer 16 to a peak current value. As the battery supply voltage $V_B$ decreases, the primary current takes longer to reach the peak value. However, the drive waveform is turned off by circuitry which senses the current through the mirror resistor R1. Therefore, the peak current in the primary will remain constant regardless of the supply voltage.

The inverter drive signal generated by the inverter drive circuit 18 under control of the microprocessor is supplied to the gate of transistor Q1. The amplitude of the inverter drive signal must be approximately 10 volts to drive the gate of the transistor Q1. In response to the 10 volt pulse of the inverter drive signal, a current is generated in the primary of the transformer 16. The level of the current $I_{PRI}$ in the primary is sensed via the mirror resistor R1 and reflected as a voltage hereinafter referred to as OVER I. The current in the mirror resistor is a known fraction (1/1000) of the current in the primary of the transformer 16. OVER I is compared in the comparator amplifier 32 with a preset reference level $I_{SET}$ of 0.4 V.

Once the OVER I voltage reaches the preset reference level, the microprocessor terminates the positive portion of the inverter drive signal via the DRIVE CONTROL signal. The current in the secondary of the transformer $I_{SEC}$ jumps to a maximum value at the maximum of the current in the primary, and then begins to decay. As a result, the voltage VC across the capacitors C1 and C2 rises in response to the current in the secondary of the transformer. However, once the current in the secondary returns to zero, the voltage across the capacitors stops rising. The signal CV representing the capacitor voltage is constantly monitored in the I/O control 22 and compared with the programmed final voltage level of the capacitors, hereinafter referred to as VUPREF. At the next occurrence of a positive pulse in the inverter drive signal, the mechanism repeats and the voltage across the capacitors C1 and C2 (VC) rises from the previously charged level to a higher level. When the voltage across the capacitors reaches the final level set by VUPREF, the comparator 38 issues a pulse as shown in FIG. 4 which is detected by the microprocessor to terminate the DRIVE signal. The level of VUPREF is programmable (via the current source 40) from 0 to 2.4 volts (DC) (or −3 volts to −0.6 volts with respect to the −3 volt reference) creating an energy output of 0.1 to 34 Joules.

The energy stored in the primary of the transformer each cycle of the drive signal is equal to $\frac{1}{2}LI_{PK}$ where L is the inductance of the primary 16a of the transformer 16. Assuming ideal conditions with ideal inductors and zero ohm switches, the on-time $t_{ON}$ is equal to $I_{PK}L/V_{BAT}$ so that $I_{PK}$ is equal to $V_{BAT}t_{ON}/L$. If the frequency of the drive signal is maintained constant, then the energy delivered to the capacitors per cycle is constant, the result being that the charge time of the capacitors is constant. The value $t_{ON}$ in the foregoing equations represents the time needed for the current in the primary ($I_{PRI}$) to reach $I_{PK}$. Particularly, because the capacitor is charged in increments (FIG. 4), the total time to charge the capacitors is the sum of the charge time for the charging increments. Thus, by ensuring that the current in the primary of the transformer reaches a peak level within a constant period of time, the charging increments are effected in a constant period of time. In effect, the battery power supply is intermittently connected to the capacitor at a fixed frequency.

Figure 5:
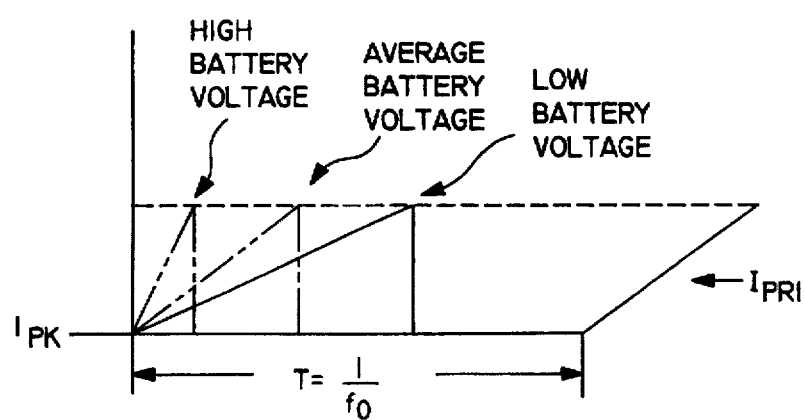
FIG. 5 illustrates a comparison of the current in the primary of the transformer when the battery is at full charge, average charge, and depleted charge.

Shown in FIG. 5 is a comparison of the current in the primary 16a of the transformer 16 at three different approximate battery voltages. When the battery is new and thus at high voltages, the current in the primary will reach the peak value more quickly than when the battery voltage is at an average level or a depleted low level. As aforementioned, however, the inverter drive signal is terminated according to the current through the mirror resistor R1 via the DRIVE CONTROL signal from the microprocessor 24. Thus the peak current will remain constant regardless of battery voltage.

The above description is intended by way of example only and is not intended to limit the present invention in any way except as set forth in the following claims.

We claim:

1. A system for controlling the charging and discharging of a defibrillation capacitor comprising:

battery supply means for providing a supply voltage;

defibrillation capacitor means for being charged to a predetermined voltage;

transformer means comprising a primary and a secondary, the secondary being connected to said defibrillation capacitor means, the secondary being charged by said primary for delivering current to the defibrillation capacitor means;

inverter means connected to said battery supply means and to the primary of said transformer means, said inverter means capable of assuming a first state in which current is supplied from the battery supply means to the primary of the transformer means and a second state in which no current is supplied to the primary;

inverter drive means connected to the inverter means for generating an inverter drive signal at least three times the value of the supply voltage comprising repeating spaced pulses, each pulse of the drive signal triggering the inverter means to assume said first state to supply current to the primary of the transformer means for a duration corresponding to a duration of each pulse;

control means connected to said defibrillation capacitor means, to said inverter means and to said inverter drive means, said control means monitoring the voltage across said defibrillation capacitor means and monitoring the current in the primary reaching a preset value, and to terminate the inverter drive signal in response to the voltage of said defibrillation capacitor means reaching said predetermined voltage; said control means controlling said inverter drive means to maintain the frequency of the inverter drive signal constant so that the energy delivered to the defibrillation capacitor means from the secondary of the transformer means per cycle of the inverter drive signal is constant;

defibrillation trigger means connected to said defibrillation capacitor means for triggering the discharge of said defibrillation capacitor means to defibrillation electrodes;

termination means connected to said defibrillation capacitor means for terminating the discharge of said defibrillation capacitor means a preset period of time after the discharge of the defibrillation capacitor means to the defibrillation electrodes by directing the charge of said defibrillation capacitor means to ground; and internal discharge means for connecting the defibrillation capacitor means to ground upon desiring not to deliver a defibrillation shock.

2. The system of claim 1, wherein said inverter means charges the primary of the transformer means in response to each pulse of the inverter drive signal so that the secondary of the transformer means supplies current to the defibrillation capacitor means during an off half cycle of the inverter drive signal when no pulse is present, the charge being built up in the defibrillation capacitor means incrementally during the off half cycle of the inverter drive signal until the predetermined voltage is reached.

* * * * *